United States Patent [19]
Burton

[11] 4,159,720
[45] Jul. 3, 1979

[54] INFUSION OF LIQUIDS INTO TISSUE

[76] Inventor: Andrew F. Burton, 1453 Whittier Pl., NW., Washington, D.C. 20012

[21] Appl. No.: 855,451

[22] Filed: Nov. 28, 1977

[51] Int. Cl.² .............................................. A61M 31/00
[52] U.S. Cl. .................................. 128/260; 128/335.5; 128/213 R
[58] Field of Search ................... 128/260, 335.5, 130, 128/213, 214, 2 R, 347, 348, 232

[56] References Cited
U.S. PATENT DOCUMENTS

| | | | |
|---|---|---|---|
| 1,242,174 | 10/1917 | Gooch | 128/213 |
| 1,276,943 | 8/1918 | Mininberg | 128/213 |
| 3,212,502 | 10/1965 | Myers | 128/335.5 |
| 3,640,269 | 2/1972 | Delgado | 128/260 X |
| 3,854,477 | 12/1974 | Smith | 128/213 |
| 3,894,538 | 7/1975 | Richter | 128/260 |
| 3,995,631 | 12/1976 | Higuchi et al. | 128/260 |
| 4,026,290 | 5/1977 | Brooker et al. | 128/260 |
| 4,054,139 | 10/1977 | Crossley | 128/260 |
| 4,077,407 | 3/1978 | Theeuwes et al. | 128/260 |

*Primary Examiner*—Robert E. Bagwill
*Attorney, Agent, or Firm*—Cushman, Darby & Cushman

[57] ABSTRACT

A means is shown for delivering a prescribed liquid medicine or other fluid to a subcutaneous tissue. The device includes a reservoir on the outside of the body for holding a supply of the prescribed liquid, the reservoir being adhesively attached to the skin near the tissue to be treated. The reservoir feeds the liquid to absorbent or capillary wicks adapted to pass through the skin to be installed in the subcutaneous tissue to which the fluid is to be fed. The wicks may be provided in several forms such as twisted or braided suture material, the ends of which, in some instances, may be encased in plastic. The wicks, in whatever form, are guided from the outside into their installed positions in the subcutaneous tissue with conventional cutting or tapered surgical needles, and in the modification making use of a plastic casing, a slightly modified needle is used to install the wick cover.

16 Claims, 17 Drawing Figures

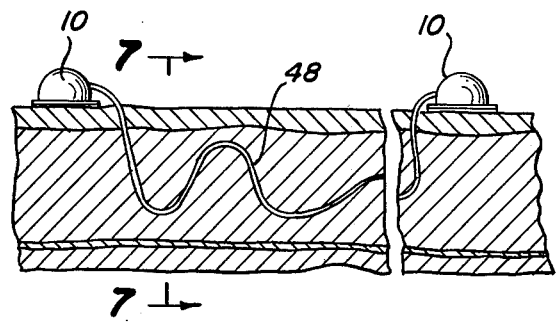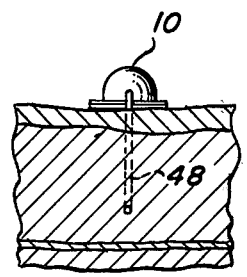
Fig.6  Fig.7
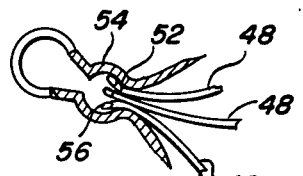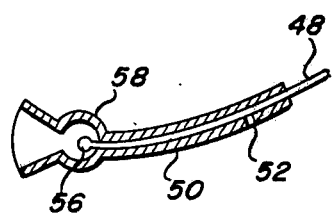
Fig.8  Fig.8a  Fig.9
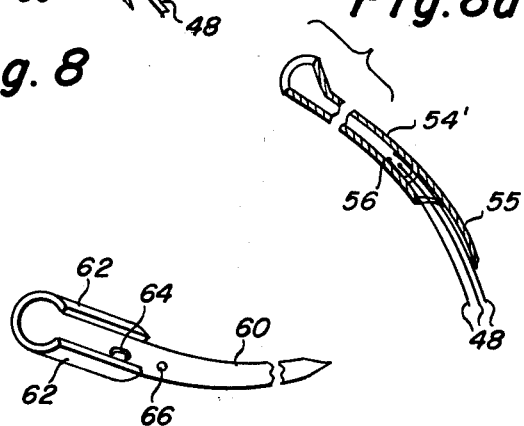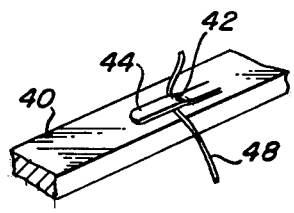
Fig.10  Fig.11
Fig.12
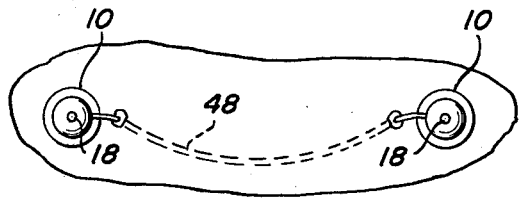
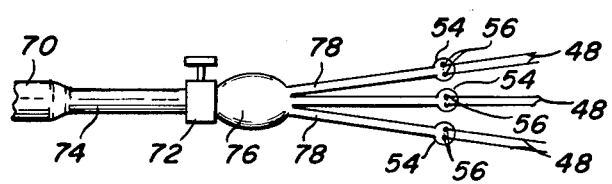
Fig.13

INFUSION OF LIQUIDS INTO TISSUE

BACKGROUND

Various devices have been used in the past to introduce a prescribed medicinal or other fluid from outside the body into subcutaneous tissue needing treatment. Injections with hypodermic needles have frequently been considered the standard means to be used for this purpose, but such injections normally cannot provide a supply of prescribed fluid in a manner to be continuously available over an extended period of time, without multiple injections and consequent puncture injuries to the body being treated.

Other means for feeding medicaments to the tissue supporting the skin are shown in the U.S. Pat. Nos. 3,814,097 to Ganderton et al, June 4, 1974 and 3,964,482 to Gerstel et al, June 22, 1976. The devices shown in these patents including skin pricking fingers or projections having a length to just pass through the skin but the projections do not pass into the subcutaneous flesh. These patents disclose applicators for feeding a drug or the like from a reservoir along or through a projection to permit a timed release of the drug under the skin but neither teaching can place the drug deeply into a subcutaneous area, for example, in the flesh between the peritoneum and the skin.

Another known time release drug applicator is shown in the two U.S. Pat. Nos. to Lee et al, 2,546,759, Mar. 27, 1951 and 2,625,158, Jan. 13, 1953, both of which show a vehicle for carrying an entire dosage of a medicine to be administered into a position under the skin for slow absorption in the body of the poultry product being treated. The dosage is positioned in an enlarged center of the device that is drawn under the skin for subcutaneous absorption. The treatment accomplished with this teaching distributes the medicine throughout the entire body of the animal and is not intended to provide nor can it normally produce a localized treatment of a given subcutaneous area.

More recently it has been proposed to feed fluids into the flesh through Teflon or stainless steel tubes having only a very limited degree of flexibility, such a procedure being shown in the U.S. Pat. No. 3,640,269 to Delgado, Feb. 8, 1972. The more or less rigid tubes shown are impervious to flow of fluid through their walls and it is necessary to attach a porous bag at the open end of the implanted tube to allow fluid to flow to or from the area of the flesh surrounding the implanted end of the tube. Such a structure allows only for a generally perpendicular insertion of a tube into a limited area of the subcutaneous flesh and would require many implantations if an extensive area were required to be treated.

BRIEF DESCRIPTION OF THIS INVENTION

The invention here shown makes use of one or more reservoir means containing a prescribed treating fluid attached to the skin of the body to be treated and one or more wicking means having a known absorption rate for the particular liquid connected to the reservoirs. The wicks of this invention are elongated, flexible elements preferably made of suture material such as silk or cotton and have either one or both of their ends immersed in the liquid stored in the reservoir means. The intermediate length of the wick is installed in the flesh to be treated with the liquid by being carried into and through the subcutaneous flesh to be positioned where desired with either conventional cutting or tapered suture needles or with a slight modification of such a needle.

The wick means can also take the form of a monofilament such as a nylon filament which is hollow with lateral perforations. Alternatively the monofilament can be solid with external grooves which are either longitudinal or spiral.

The wick means can be implanted as a single strand or a plurality of wicks can be installed to cover a more widespread are for delivery of a fluid such as might contain an antibiotic or anesthetic or other solution. The wicks can be strands of any conventional form that will absorb or convey by capillary action an appreciable quantity of the fluid to be used for the treatment of the tissue. The wick means can be selected to deliver a known rate of the prescribed fluid into the flesh in which the wick has been installed.

The wick can be used not only for delivery of the prescribed fluid into an exact area where it may be needed, but the wick means may also be installed in a manner to serve the double purpose of not only delivering the fluid where needed and as an actual suture to hold the flesh together while the wound is mending, which action is promoted by the presence of the desired prescribed fluid directly in the area where treatment is most effective.

IN THE DRAWINGS

FIG. 6 is a sectional side elevation looking from the head of a person toward his feet at a typical wick installed in the living subcutaneous flesh, for example, between the skin and peritoneum layers in the abdominal area of a man;

FIG. 7 is a view looking along line 7—7 of FIG. 6;

FIG. 8 is a detail perspective of a connector for attaching a plurality of wicks to the reservoir shown in FIGS. 1 and 3;

FIG. 8a is an alternate form or modification of the connector shown in FIG. 8;

FIG. 9 is a connector for attaching one of a number of a modified form of wick means to the reservoir shown in FIGS. 1 and 3;

FIG. 10 is a perspective view of a needle means for leading the modified form of wick shown in FIG. 9 into the flesh to be treated;

FIG. 11 is a detailed view of a connecting means for holding the ends of another form of the wick means in the reservoir shown in FIGS. 4 and 5;

FIG. 12 is a plan view showing a wick means installed subcutaneously;

FIG. 13 is a plan view of still another form of connector having a valve feed and finger operated pumping bulb to force feed fluid to the wicks;

DETAILED DESCRIPTION

Figure 1:
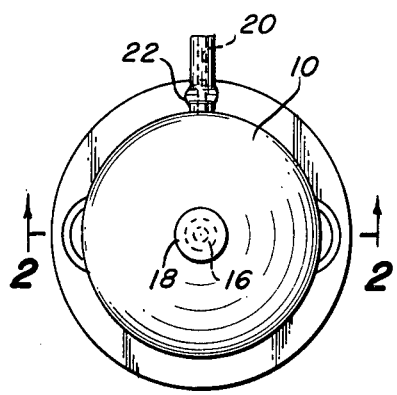
FIG. 1 is a plan view of a reservoir adapted for use with a wick of this invention.
Figure 2:
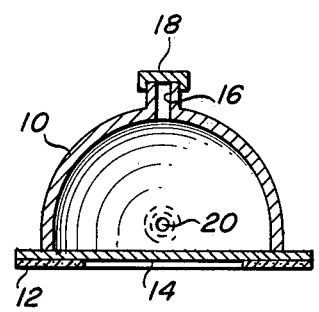
FIG. 2 is a view taken on line 2—2 of FIG. 1.

A typical use of the present invention is shown in the drawings wherein a reservoir 10 for a prescribed liquid is shown attached to the abdominal area of a person to be treated as illustrated in FIGS. 6 and 12. In this form of the invention, the details of the two reservoir structures 10 shown in FIG. 12, can be seen in FIGS. 1 and 2. The reservoirs are adhesively secured to the skin of the patient with a suitable non-reactive adhesive 12 applied as a band around the periphery of the bottom 14 of the reservoir. The reservoir 10 is dome-shaped and is designed to be filled with a prescribed liquid to be administered subcutaneously. The dome has a filling opening 16 at its top adapted to be sealed with a cap 18 and the opening is designed to cooperate with a standard syringe hub to maintain sterile conditions during filling. A suitable outlet opening 20 is provided adjacent the floor 14 for permitting fluid to flow from the reservoir to a wick means for distribution in the tissue to be treated and a configured hub 22 surrounds the outlet 20 to support an attaching and sealing means that cooperates with one end of the wick means.

The reservoir 10 has a single outlet for supporting and feeding fluid to one or more wicks, as will appear more fully below, and may be made of any suitable inert material such as rubber, plastic or even metal. The reservoir may be formed to other shapes as shown in FIGS. 3 and 4, which forms of reservoirs may have a plurality of outlet openings for connection to a multiplicity of wicks if a larger area of tissue is to be treated with an antibiotic or anesthetized, for example.

Figure 3:
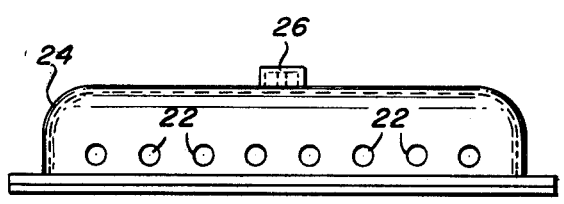
FIG. 3 is a side view of a modified reservoir means adapted to cooperate with a plurality of elongated wick means.

The reservoir 24, shown in FIG. 3, provides an elongated chamber similar in construction otherwise to the dome-shaped reservoir 10. Reservoir 24 has a covered infeed 26 for cooperation with a syringe for filling it with fluid and a plurality of configured hub outlets 22 for connection to means for attaching and sealing the wick means to the outlets for dispensing fluid contained in the reservoir.

Figure 4:
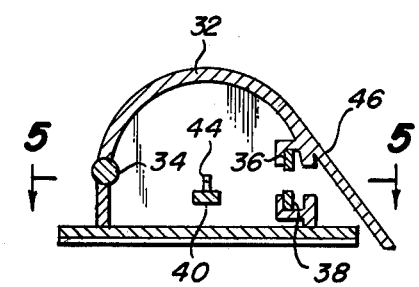
FIG. 4 is a sectional end view of still another form of reservoir means with a hinged cover shown partly open, that is adapted for use in this invention.

The reservoir 30, shown in FIG. 4, is elongated like the reservoir 24 but is different in that it has a hinged cover 32, shown in a partly opened position, that pivots about hinge 34. The cover 32 is designed to be closed over the reservoir to provide a fluid-tight seal and includes two foam plastic lips 36 and 38 that meet along one side to seal that edge of the reservoir. A mounting bar 40 is supported inside the reservoir by its end walls to extend lengthwise through the body thereof in a direction generally parallel to the lips 36 and 38 to provide a terminal support means for holding the ends of the wicks submerged in the fluid stored in the reservoir. The connection for the ends of the wicks with the bar 40 is illustrated in FIG. 11, the bar having a plurality of horseshoe shaped depressions 42 spaced apart along its length with their open sides facing toward the lip 38. Each depression has a mushroom-shaped pin 44 centered therein and formed integral with bar 40 to serve as anchor posts for the ends of the elongated wicks that are draped over the lip 38 to carry liquid from the reservoir to the tissue to be treated. The cover 32 may be closed onto the wicks which are then engaged between lips 36 and 38 to seal the fluid to be carried from the reservoir by the wicking action into the tissue. The cover 32 is provided with a flexible flap 46 on its front side that is adapted to cover the joint between sealing strips 36 and 38 and hold the wicks against the reservoir. The flap 46 should be of a length to also cover part of the wound and prevent the gauze dressing from touching the wet wicks.

The reservoir structure can be made in another form, with a removable cover adapted to be supported on the reservoir body with a fluid-tight seal and the various types of reservoirs can be provided with other outlet means for supporting one end of each of the wicking means in contact with the liquid to be absorbed thereby and delivered into the tissue to be treated. The reservoirs may be constructed in various curved shapes to provide for a more comfortable attachment to various surfaces of the body to be treated. It is important only that the several reservoir means, their filling openings and their outlets adapted for connection to the wicks or that the leaders for the wicks that pass into the reservoir, be constructed so that they may be made sterile and that the reservoirs themselves be made sterile for reception of the treating fluid.

The wicks themselves preferably take the form of an elongated flexible suture-like material 48, as best shown in FIGS. 6, 8 and 12, adapted to be installed in the subcutaneous flesh with any conventional form of curved cutting or tapered suture needle. The wick shown in FIG. 6 was led into its installed position as if it were a suture and indeed in one use to which the invention may be put, the wick serves as a suture for holding the severed flesh together as well as a carrier or conduit for delivering fluid antibiotic or anesthetic substances and the like, directly to the affected area.

The wicks may be made of an absorbent suture material such as silk or cotton that is braided, woven or otherwise formed of a length to reach from the reservoir into the tissue to be treated or as shown in FIG. 12, from one reservoir, through the tissue and out of the body, to be connected to a second reservoir. The woven wick can be formed to a tubular or other cross-sectional shape, whichever shape and tightness of weave serves to best absorb or wet the wick to carry the fluid by capillary action along the length of the wick from the reservoir into contact with the tissue. The suture material may be further twisted or woven to include a copper thread for electrophoresis to increase wick flow by attaching the suture into an electrical battery system.

Figures 14, 15, 16:
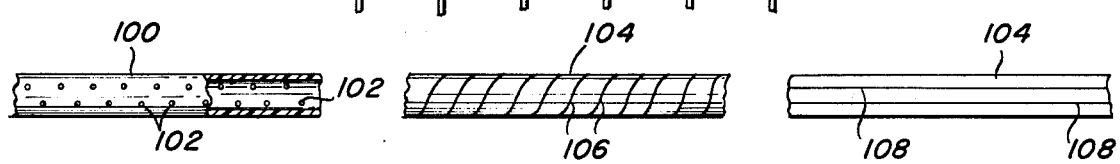
FIG. 14 is a side view, on an enlarged scale, of a hollow perforated wick.
FIG. 15 is a side view, on an enlarged scale, of a spirally grooved wick.
FIG. 16 is a side view, on an enlarged scale, of a longitudinally grooved wick.

As shown in FIG. 14 the wick may have the form of a hollow monofilament 100 of fore example nylon, provided with lateral perforations 102 through which the fluid will pass into the tissue. As shown in FIG. 15 the wick may also have the form of a solid filament 104 having spiral grooves 106 in its external surface. As shown in FIG. 16 the filament 104 may have longitudinal groove 108.

In some instances to prevent a premature loss of absorbed fluid from the wick, the lead in end of the wick between the reservoir and along its length up to the area of the tissue to be treated, may be encased in a plastic sleeve 50, as shown in FIG. 9. The tube 50 has a small aperture 52 formed in one end thereof for use during the installation of the encased wick as will appear more fully below. It is apparent that the sleeve 50 can be provided with several other perforations throughout its length if a controlled but smaller release of fluid from the wick is desired along the lead in portion of the wick.

Several means are illustrated for attaching the wicks to the reservoirs. As shown in FIG. 8, one or more wicks 48 may be supported in a central aperture 52 formed in a somewhat resilient bulb 54 adapted to be stretched to fit snugly onto the configured hubs 22 shown in FIGS. 1 and 3. The bulb 54 has skirt integral therewith to provide a sterile snap-on fit over the hub and the enlarged ends 56 of the wicks 48 that are confined in bulb 54 are immersed in the fluid filled into the reservoirs 10 and 24. The ends of the wicks absorb the fluid that is gradually fed along the length of the wick by absorption or capillary action. When the wick has been installed in the tissue to be treated, the prescribed fluid is thus fed from the reservoir into the tissue.

In FIG. 8a a modification of the connector of FIG. 8 is shown. In this alternate structure the bulb 54' is elongated to permit the reservoir to be placed on the body as far as two or three feet from the wound and the end of the connector is provided with a cover 55 of a length and configuration that is adapted to overlie the length of suture leading from the connector to the wound to prevent fluid loss from the suture and to prevent the gauze dressing over the wound from absorbing liquids from the wicks. The individual wicks 48 pass through suitable apertures in the end wall of the connector and are provided with enlarged heads 56 as described above with respect to FIG. 8.

In FIG. 9 that bulbous end 58 at the end of the plastic cover 50 for the wick is adapted to snap onto the hubs 22. The liquid from the reservoir flows out hub 22 to saturate the enlarged end 56 of the wick so fluid can flow along the wick within the confines of the plastic tube 50 to emerge into the tissue into which the wick has been implanted.

Figure 5:
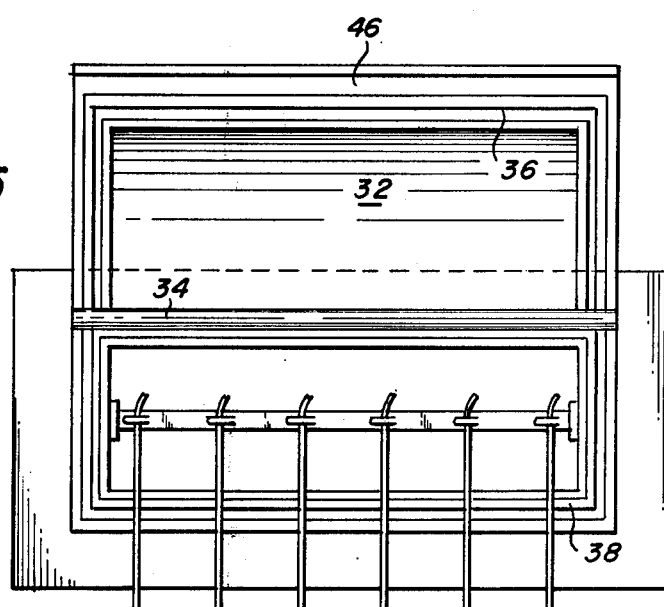
FIG. 5 is a view taken on line 5—5 of FIG. 4.

The wick attaching means shown in FIGS. 4, 5 and 11 utilizes the metallic tang 44 raised above the surface, but integral with bar 40. The wicks 48 may be frictionally engaged in the bight 42 between bar 40 and tang 44 to hold the wick in place. The cover 32 of the reservoir may then be closed and the reservoir filled with fluid to wet these wicks.

The wicks are adapted to be installed in the flesh to be treated by means of conventional suture needles. These needles may be selected from the conventional cutting or tapered needle design and the wicks are pulled through the skin and into the subcutaneous tissue in the same way in which sutures are placed in the flesh. As shown in FIG. 6, a wick can be installed in a serpentine path to reach a substantial area of tissue to be treated. In some cases it may be desirable to install a plurality of wicks in side by side relation to provide for feeding a continuous supply of a prescribed fluid to a much more extensive subcutaneous area. The wick illustrated in FIG. 6 has a greater ability to dispense fluid within a wider area than when a wick is fed by only one reservoir, and as there shown, the wick is connected at its opposite ends to separate reservoirs 10 so the fluid can flow into the tissue to be treated from two directions.

When a wick having a plastic covering like that shown in FIG. 9 is to be installed in the flesh, a special needle, as illustrated in FIG. 10, may be used. This needle has a curved body 60 with a flexible barrel-shaped end 62 integral with its trailing end. The barrel has a slit 62 lengthwise to permit the end of the plastic cover 50 of FIG. 9 to be releasably engaged in the barrel. The end of the wick that has been fed through plastic cover 50, is pulled through aperture 66 in the needle. The end of the plastic cover is held in the barrel 62 temporarily and a pin 64 integral with the needle, fits into aperture 52 in the end of the plastic cover to pull the wick and the plastic cover through the skin and into the subcutaneous tissue. When the plastic cover has been pulled in to the flesh to reach the edge of the tissue to be treated, the needle is separated from the plastic cover by manipulating these elements through the skin to disconnect the plastic cover from pin 64 and then the needle may be pulled free. The wick is still engaged in the eye 66 of the needle and may be led through the flesh as it is pulled through the plastic cover to be installed in the tissue to be treated. After the plastic cover has been used to assist in feeding the wick into its installed position, and the cover has been disconnected from the needle, the cover with the enlarged end of the wick held in bulb 54 can be connected to a reservoir outlet.

The reservoir and wick means described above can be used as shown in FIG. 6 to feed a prescribed liquid to a subcutaneous tissue from each end of the wick. In other applications the wick may be detached from the needle after the wick has been led deeply into the tissue to leave only one end of a wick connected to one reservoir. As suggested above, a plurality of wicks can be simultaneously installed in tissue to be treated or a single wick can be used.

Referring to FIG. 13, another arrangement is shown for feeding fluid to the wicks. The resilient bulb 70 is adapted to be fitted onto the outlet 70 of one of the reservoirs to direct fluid to the valve 72 at the end of the conduit 74 that may be of any desired length. The valve 72 may be of any conventional type manual or ball check valve and is opened to permit flow into the resilient bulb pump device 76 of from one to five cubic centimeter capacity and after the bulb 76 is filled, valve 72 is closed and the bulb 76 is operated to force fluid into one or more tubes 78 to be fed under pressure into one or more bulbs 54 to which sutures 48 are connected. The liquid may be force fed to these sutures to increase the flow of fluid into the wound and to deliver fluid from a reservoir situated some distance from the wound to ensure a sufficient flow of medicine to the affected area.

The reservoirs are individual units well adapted to be maintained in sterile condition and to be filled from time to time without destroying their sterility so that a prolonged treatment of the subcutaneous tissue can be accomplished. The wicks are likewise designed to be connected to the reservoirs in a manner to preserve the sterility of the system so that a prescribed liquid can be continuously delivered at a controlled rate to the tissue to be treated.

While the above includes a description of the preferred from and operation of this invention, it is possible that others may conceive of other structures utilizing its essential characteristics, that will fall within the scope of the following claims.

What is claimed is:

1. A means for treating the living subcutaneous tissue of a body, the means including wick means for continuously delivering a medicinal or other prescribed fluid from temporary reservoir means in which the liquid is stored, said reservoir means having a surface contoured to a portion of and releasably attached to that portion of the body containing the tissue to be treated, comprising an elongated flexible wick means of substantial length which is adapted to be installed in the tissue to be treated, said wick means having a known rate of absorption for said fluid to feed fluid into said tissue, at least one end of said wick means being in contact with the fluid in said reservoir means, needle means for engaging with the other end of said wick means to lead said wick means into its installed position and then be disconnected from the wick means, and said wick means following in the path through which said needles means is guided during installation of the wick means in the tissue so that the wick means is led to a desired position so as to feed the absorbed fluid directly to the area in the tissue needing attention.

2. A means as described in claim 1 wherein said wick is made of braided silk suture material.

3. A means as described in claim 1 wherein said wick is made of braided cotton suture material.

4. A means as described in claim 1 wherein said wick is a closely woven silk material.

5. A means as described in claim 1 wherein said wick is a closely woven cotton material.

6. A means as described in claim 4 wherein said wick is woven to have a hollow cylindrical cross-sectional shape.

7. A means as described in claim 5 wherein said wick is woven to have a hollow cylindrical cross-sectional shape.

8. A means as described in claim 1 wherein a plurality of reservoir means are attached to said body in spaced apart positions and the opposite ends of said elongated wick means are submerged respectively in the fluid stored in said spaced apart reservoir means after said wick is installed in the tissue.

9. A means as described in claim 1 wherein a plurality of wick means are installed in said tissue and communicate with said reservoir means.

10. A means as described in claim 8 wherein a plurality of said wick means are installed in said tissue and each wick has its respective opposite ends submerged in the fluid stored in said spaced apart reservoir means.

11. A means as described in claim 1 wherein the portion of the length of said wick means positioned between said reservoir means and said tissue to be treated is encased in a closely fitting cylindrical plastic cover.

12. A means as described in claim 11 wherein said plastic cover is of a length to extend into the tissue to be treated, said casing being perforated where it is installed in said tissue.

13. A means as described in claim 11 wherein said plastic cover is adapted to be temporarily attached to said needle means while being installed in said tissue and the plastic cover is then disconnected from the needle means and the portion of the wick means not covered by the plastic is installed in the tissue.

14. A means as described in claim 1 wherein said reservoir means has a filler opening and a cap therefor, said reservoir being contoured to comfortably engage against the body, said reservoir means having feed opening means therein and a ring of non-reactive adhesive around its periphery for engagement with the body, and means cooperating with said feed opening means for connecting said wick means to said reservoir to place the wick means in contact with liquid stored in the reservoir means.

15. A means as in claim 1 wherein the wick means is a hollow laterally perforated filament.

16. A means as in claim 1 wherein the wick means is a filament having grooves in its external surface.

* * * * *